United States Patent [19]

Krogh

[11] Patent Number: 4,484,001

[45] Date of Patent: Nov. 20, 1984

[54] METHOD FOR PREPARING N-BENZYLOXYCARBONYL AMINO ACIDS CONTAINING ADDITIONAL FUNCTIONALITY

[75] Inventor: James A. Krogh, Mount Prospect, Ill.

[73] Assignee: PPG Industries, Inc., Pittsburgh, Pa.

[21] Appl. No.: 553,214

[22] Filed: Nov. 18, 1983

[51] Int. Cl.³ .................................... C07C 125/065
[52] U.S. Cl. ........................ 560/160; 260/112.5 R; 548/533; 560/29; 560/148; 560/159
[58] Field of Search ............... 560/29, 148, 159, 160; 260/112.5 R; 548/533

[56] References Cited

U.S. PATENT DOCUMENTS

| | | | |
|---|---|---|---|
| 3,532,736 | 10/1970 | Chamberlin | 560/160 |
| 3,562,295 | 2/1971 | Pedersen | 260/338 |
| 3,592,836 | 7/1971 | Ugi | 560/163 |
| 3,686,225 | 8/1972 | Pedersen | 260/340.3 |
| 3,687,978 | 8/1972 | Pedersen | 260/340.3 |
| 3,808,190 | 4/1974 | Dahlmans | 260/112.5 R |
| 3,847,949 | 11/1974 | Pedersen et al. | 260/340.3 |
| 3,875,207 | 4/1975 | Iselin | 560/160 |
| 3,997,562 | 12/1976 | Liotta | 260/338 |
| 4,033,998 | 7/1977 | Harris | 560/160 |
| 4,293,706 | 10/1981 | Gorman et al. | 560/163 |
| 4,345,091 | 8/1982 | Sugiyama | 560/163 |
| 4,450,284 | 5/1984 | Sathe | 560/163 |

OTHER PUBLICATIONS

G. W. Gokel et al., "Principles and Synthetic Applications in Crown Ether Chemistry", *Synthesis*, pp. 168-184 (1976).
B. Arkles et al., "Silacrowns:Phase-Transfer Catalysts", *Organometallics*, vol. 2, No. 3, pp. 454-457 (1983).
Petrarch Systems, Inc., Product Data Sheet, "Silanes for Phase Transfer Catalysis".
Anon., "A New Generation of Antibiotics", *Science*, vol. 213, p. 1238 (1981).
H. Breuer et al., "Monocyclic β-Lactam Antibiotics . . . ", Abstract-878, 21st Interscience Conference on Antimicrobial Agents and Chemotherapy (1981).
D. M. Floyd et al., "Monobactams . . . "*Journal of Organic Chemistry*, vol. 47, pp. 176-178 (1982).
A. L. Lehninger, *Biochemistry*, 2nd Edition, Worth Publishers, Inc., New York, pp. 71-83 (1975).
E. Wertheim, *Textbook of Organic Chemistry*, 3d Edition, McGraw-Hill Book Co., Inc., New York, pp. 808-810 (1951).
C. M. Starks et al., *Phase Transfer Catalysts—Principles and Techniques*, Academic Press, New York, pp. 77-90 (1978).
C. M. Cimarusti et al., "Monobactams . . . " *Journal of Organic Chemistry*, vol. 47, pp. 179-180 (1982).
McOmie, "Protective Groups in Organic Chemistry," pp. 56-60 (1973).
Greenstein, "Chemistry of the Amino Acids," vol. 2, pp. 887-901 (1961).
Bergmann, Ber., 65B, pp. 1192-1201 (1932).

*Primary Examiner*—Michael L. Shippen
*Attorney, Agent, or Firm*—George D. Morris

[57] ABSTRACT

Crown ethers and silacrown ethers are employed as phase-transfer reagents in blocking primary amino functionality of alkali metal salts of amino acids with a benzyloxycarbonyl group.

20 Claims, No Drawings

METHOD FOR PREPARING N-BENZYLOXYCARBONYL AMINO ACIDS CONTAINING ADDITIONAL FUNCTIONALITY

BACKGROUND OF THE INVENTION

Amino acids are often employed as raw materials in the preparation, by a sequence of reactions, of compounds having various uses. In many of these sequences it is necessary to reversibly block a primary amino group of the amino acid or its salts in order that the blocked compound may undergo further reactions which would otherwise irrevocably destroy the amino group, and yet permit later regeneration of the primary amino group.

Benzyloxycarbonyl is eminently suited as the blocking group for these purposes. See for example, U.S. Pat. No. 4,293,706, Floyd et al, "Monobactams...", *Journal of Organic Chemistry*, Vol. 47, No. 1, pages 176–178 (1982), Cimarusti et al, "Monobactams...", *Journal of Organic Chemistry*, Vol. 47, pages 179–180, and Wertheim, *Textbook of Organic Chemistry*, 3d edition, pages 808–809 (1951), the entire disclosures of which are incorporated herein by reference. The benzyloxycarbonyl group may be introduced by reacting alkali metal salt of the amino acid with a benzylhaloformate, such as benzylchloroformate of benzylbromoformate, in a polyphase reaction mixture.

When the amino acid contains, in addition to a primary amino group and at least one carboxylate anion, at least one fuctional group selected from the class consisting of hydroxyl, additional primary amino, secondary amino, primary imido, and primary amido, product yields are reduced due to the undesired side reaction of the benzylhaloformate with the additional functionality. A hydroxyl group, for instance, can and often does react with the benzylhaloformate to form an undesired carbonate. It is important to observe that loss of product by this mechanism pertains only to those amino acids containing the additional functionality; it does not pertain to those amino acids which do not contain the additional functionality.

Crown ethers and silacrown ethers are known phase-transfer reagents which have been employed for various reactions. See, for example U.S. Pat. Nos. 3,562,295; 3,686,225; and 3,687,978; and Gokel and Durst, "Principles and Synthetic Applications in Crown Ether Chemistry", *Synthesis*, March 1976, pages 168–184; Starks and Liotta, *Phase Transfer Catalysts-Principles and Techniques*, Academic Press, New York, pages 77–90 (1978); Arkles et al, "Silacrowns: Phase-Transfer Catalysts", *Organometallics*, Vol. 2, No. 3, pages 454–457 (1983); and *Product Data Sheet, Silanes for Phase Transfer Catalysis*, Petrarch Systems, Inc., Bristol, Pa., the entire disclosures of which are incorporated herein by reference. Neither the crown ethers nor the silacrown ethers have, however, been employed as phase-transfer reagents in blocking a primary amino group of an amino acid having the additional functionality discussed above.

THE INVENTION

It has now been discovered that when a crown ether or a silacrown ether is employed as a phase-transfer reagent in blocking a primary amino group of an alkali metal salt of an amino acid having the additional functionality heretofore described, the undesired side reaction of the benzylhaloformate with the additional functionality is greatly reduced. In other words, use of the crown ether or the silacrown ether markedly and unexpectedly increases the specificity of the reaction producing the desired product. As a consequence, yields of the desired product are considerably increased. In the method, therefore, wherein alkali metal salt of an amino acid which is devoid of tertiary amino groups and quaternary ammonium groups, and which contains in addition to a primary amino group and at least one carboxylate anion, at least one functional group selected from the class consisting of hydroxyl, additional primay amino, secondary amino, primary imido, and primary amido, is reacted with benzylhaloformate selected from the group consisting of ring-substituted benzylchloroformate, ring-unsubstituted benzylchloroformate, ring-substituted benzylbromoformate, and ring-unsubstituted benzylbromoformate in a polyphase reaction mixture comprising an organic liquid phase and an aqueous liquid phase to produce alkali metal salt of an N-benzyloxycarbonyl amino acid in which the aromatic ring of the benzyl is substituted or unsubstituted and which contains the functional group, the invention is the improvement comprising conducting the reaction in the presence of phase-transfer reagent comprising crown ether, silacrown ether or a mixture thereof.

Unless otherwise qualified or evident from its context, the nomenclature used herein for the various groups is without regard to whether they are protonated, neutral, or deprotonated.

Amino acids, the alkali metal salts of which are used as reactants in the present invention, are widely varied. They may be polypeptides of one, two, three, four, five, or more fundamental amino acids units, at least one of which contains the additional functionality described above. More usually, however, they are the fundamental amino acids themselves which contain the additional functionality. Examples include serine, threonine, tyrosine, lysine, arginine, 4-hydroxyproline, 5-hydroxylysine, ε-N-methyllysine, homoserine, ornithine, canavanine, asparagine, glutamine, citrulline, and djenkolic acid. Fundamental amino acids containing hydroxyl functionality are preferred. Examples include serine, threonine, tyrosine, 4-hydroxyproline, 5-hydroxylysine, and homoserine.

The amino acids may individually have the L-configuration or the D-configuration, although the L-configuration is more common. Mixtures of amino acids, including racemic mixtures, may also be used.

The alkali metal salts of amino acids generally employed are those of lithium, sodium, or potassium. Ordinarily sodium or potassium is used. Sodium is preferred.

When substituted benzylchloroformate or substituted benzylbromoformate is employed as a reactant, the numbers and identies of the substituents are such that they do not render the benzylhaloformate unsuitable for its intended purpose. Examples of substituents which may be used include nitro, methyl, methoxy, chloro, and the like. While more than one substituent may be on the ring, and while the substituents may be the same or different, generally only one substituent is present, and this is often, but not necessarily, located in the 4-position. As between the substituted benzylchloroformates and the substituted benzylbromoformates, the former are more often used.

Unsubstituted benzylchloroformate and unsubstituted benzylbromoformate are preferred for use in the invention. Unsubstituted benzylchloroformate is especially preferred.

The crown ethers are macroheterocycles containing repeating

units. The silacrown ethers are crown ethers in which one

unit has been replaced by an

unit. The crown ethers are named in the format "number-crown-number" where the first number is the total number of atoms in the ring and the second number is the total number of oxygen atoms in the ring. The substitution of other units for some of the ethanediyl groups of the ring precedes the basic format. As examples, the compound

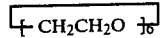 (I)

is denoted 18-crown-6 while the commpound

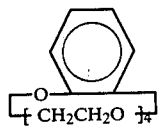 (II)

is denoted benzo-15-crown-5. The silacrown ethers are identified similarly using the prefix "sila". Thus the compound

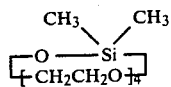 (III)

is denoted 1,1-dimethylsila-14-crown-5.

The preferred phase-transfer reagents used in the present invention are those represented by the formula

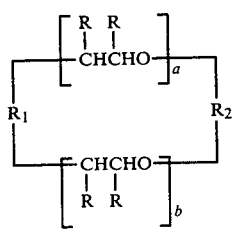 (IV)

wherein
a. $R_1$ is

b. $R_2$ is

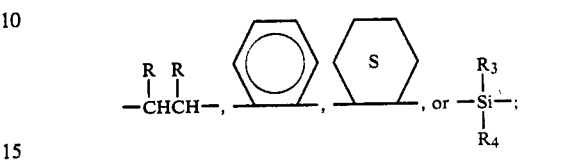

c. $R_3$ is methyl, ethyl, methoxy, ethoxy, vinyl, an organic polymeric substrate, or an inorganic polymeric substrate;
d. $R_4$ is methyl, ethyl, methoxy, or ethoxy;
e. each individual R of said phase-transfer reagent is independently hydrogen, methyl, ethyl, methoxy, ethoxy, vinyl, or phenyl;
f. The value of a is in the range of from 0 to 4; and
g. the value of b is in the range of from 1 to 4.

Silacrown ether may be attached to a polymeric organic substrate in many ways. In one embodiment, a vinyl-functional silacrown ether is addition polymerized with one or more ethylenically unsaturated monomers such as alkyl acrylates, alkyl methacrylates or styrene using well known free radical addition polymerization techniques. Similarly, silacrown ether may be attached to inorganic polymeric substrates, especially silicious substrates, in various ways. As an example 1-methyl-1-methoxy-silacrown ether may be reacted with surface hydroxyl of a glass substrate to attach the silacrown ether to the glass through a siloxane bond and produce methanol as a byproduct. The polymeric substrate, whether organic or inorganic, serves to immobilize the silacrown ether. In some applications this produces distinct advantages, including ease of removal of the phase-transfer reagent from liquid reaction mixtures as for example by filtration or centrifugation.

In Formula IV, often the value of a is in the range of from 1 to 4 and the value of b is in the range of from 1 to 4. Preferably, the value of a is in the range of from 1 to 2 and the value of b is in the range of from 1 to 2.

The preferred phase-transfer reagents are the crown ethers. The crown ethers most often used are those represented by the formula

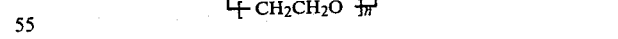 (V)

where the value of n is in the range of from 3 to 10. Frequently the value of n is in the range of from 4 to 8. The particularly preferred crown ethers are those wherein the value of n in Formula V is in the range of from 4 to 6, that is to say, 12-crown-4, 15-crown-5 and 18-crown-6.

The reaction of the alkali metal salt of the amino acid and the benzylhaloformate is conducted in a polyphase reaction mixture comprising an organic liquid phase and an aqueous liquid phase. In some instances, especially those in which the phase-transfer is essentially insoluble in the liquid phases, a solid phase is also present.

The reaction may be carried out batchwise, continuously, semibatchwise, or semicontinuously.

Although extrinsic organic solvent is not ordinarily employed, it may be used when desired. Examples of suitable extrinic organic solvents include benzene, toluene, xylene, chlorobenzene, nitrobenzene, pentane, hexane, heptane, petroleum ether, tetrahydrofuran, diethyl ether, methylene chloride, chloroform, carbon tetrachloride, and 1,2-dichloroethane. Only one extrinsic organic solvent, a plurality of extrinsic solvents or no extrinsic organic solvent may be used. Usually, but not necessarily, the extrinsic solvent is inert under the conditions of the reaction.

The temperatures at which the eaction is conducted may vary considerably, but usually they are in the range of from about -31 10° C. to about +60° C. Temperatures in the range of from about +5° C. to about +30° C. are preferred.

The reaction is ordinarily conducted at or near ambient atmospheric pressure, although greater or lesser pressures may be used where desired.

The pH of the aqueous phase of the reacton mixture during the reaction is best discussed in terms of the $pK_2'$ value of the amino acid whose alkali metal salt is employed as a reactant. The $pK_2'$ values of amino acids and their determination are described by Lehninger, *Biochemistry*, 2d Edition, pages 71-81 (1975), the entire disclosure of which is incorporated herein by reference. Each amino acid has a characteristic $pK_2'$ value, and the $pK_2'$ values of the common amino acids are well established. See, for example, Lehninger, supra, and *The Merck Index*, 9th Edition (1976).

The pH of the aqueous phase of the reaction mixture during the reaction may vary considerably, but usually the pH is in the range of from about $(pK_2'+2)$ to about $(pK_2'-2)$. Often the pH is in the range of from about $(pK_2'+1.5)$ to about $(pK_2'-1.5)$. Typically the pH is in the range of from about $pK_2'$ to about $(pK_2'+1.5)$. From about $pK_2'$ to about $(pK_2'+1)$ is preferred.

The reaction is conducted by admixing the benzylhaloformate, an aqueous solution of the alkali metal salt of the amino acid, and the phase-transfer reagent while maintaining the pH of the aqueous phase in the desired range. Ordinarily, but not necessarily, the phase-transfer reagent is admixed with the aqueous solution and then the benzylhaloformate is added while the pH of the aqueous phase is maintained by the generally concurrent addition of aqueous alkali metal hydroxide solution as a separate stream. After completing the additon of benzylhaloformate to the reaction mixture, agitation and addition of aqueous alkali metal hydroxide are continued until essentially complete reaction of the benzylhaloformate occurs as indicated by stabilization of the pH. Stabilization of pH is indicated when no additional alkali metal hdyroxide is required to be added to the reaction mixture to maintain the pH within the desired range.

The molar ratio of the benzylhaloformate to the alkali metal salt of the amino acid ultimately employed may vary considerably, but usually it is in the range of from about 0.9:1 to about 1.3:1. Often molar ratio is in the range of from about 1:1 to about 1.2:1. Preferably it is in the range of from about 1:1 to about 1.05:1.

The equivalent ratio of the phase-transfer reagent to the alkali metal salt of the amino acid ultimately employed may also vary considerably. Typically the equivalent ratio is in the range of from about 0.001:1 to about 0.1:1. Often the equivalent ratio is in the range of from about 0.001:1 to about 0.01:1. From about 0.002:1 to about 0.005:1 is preferred.

The product of the reaction, namely, alkali metal salt of an N-benzyloxycarbonyl amino acid, may be recovered from the reaction mixture when this is desired. More commonly, however, the reaction mixture is acidified, usually with cooling, to convert the product to the free amino acid. Examples of acids that can be used for the acidification include hydrochloric acid, hydrobromic acid, sulfuric acid, nitric acid, phosphoric acid, boric acid, and acetic acid. It is preferred to use the hydrohalic acid corresponding to the benzylhaloformate originally employed so as not to introduce a further anionic species to the reaction mixture. Acidification can be conducted to any desired pH, but ordinarily the final pH of the reaction mixture is in the range of from about 1 to about 4. Preferably the final pH is in the range of from about 1.5 to about 3. In most instances as the acidfication progresses, a pH is reached where the N-benzyloxycarbonyl amino acid begins to precipitate. Continued acidification then results in further precipitation until the reaction mixture is nearly exhausted of amino acid.

The temperatures at which acidification may be conducted may vary considerably, but usually they are in the range of from about −10° C. to about +60° C. Temperatures in the range of from aboout +5° C. to about +20° C. are preferred.

The acidification is ordinarily conducted at or near ambient atmospheric pressure, although greater or lesser pressures may be used where desired.

The precipitated amino acid may be separated from its mother liquor by conventional procedures such as decantation, filtration, or centrifugation. In a preferred embodiment, however, the precipitate is dissolved by adding an organic solvent, such as for example, ethyl acetate, diethyl ether, toluene, tetrahydrofuran, and bis(2-methoxyethyl) ether, to the reaction mixture. After the organic and aqueous phases have been separated, the N-benzyloxycarbonyl amino acid may be recovered by any conventional procedure, as for example, by solvent-stripping and drying.

The N-benzyloxycarbonyl amino acids produced by the process of the present invention have many and varied uses. They may, for example, be used in the preparation of polypeptides by the Bergman method. Many of them, as for example, N-benzyloxycarbonyl-L-threonine and N-benzyloxycarbonyl-L-serine, may be used in the preparation of monocyclic $\beta$-lactem antibiotics, commonly known as monobactams.

When further reaction products have been produced from the N-benzyloxycarbonyl amino acid or alkali metal salt thereof, the benzyloxycarbonyl group may be removed to restore the original primary amino functionality. This is usually accomplished by catalytic hydrogenation or sometimes by hydrolysis.

The invention is further described in conjunction with the following examples which are to be considered illustrative rather than limiting, and in which all parts are parts by weight and all percentages are percentages by weight unless otherwise specified.

EXAMPLE I

This is a comparative example showing the effect of using no phase transfer catalyst in the preparation of N-benzyloxycarbonyl-L-threonine.

A 2-liter, 5-necked reaction flask equipped with a thermometer, a mechanical agitator, a pH electrode, and two constant-volume addition funnels was charged with 119.2 grams of L-threonine (98%) and 600 grams of water. Eighty grams of 50% aqueous sodium hydroxide solution was then added to convert the amino acid to the sodium salt. The reaction mixture then had a pH of about 11.3. The additions of 174.0 grams of benzylchloroformate (99%; hereinafter "BCF"), 80 grams of 50% aqueous sodium hydroxide solution (hereinafter "caustic solution") and concentrated hydrochloric acid (hereinafter "HCl acid") as separate streams were accomplished according to Table 1.

TABLE 1

| Time, hours:minutes | Temperature, °C. | pH | Remarks |
|---|---|---|---|
| 0:00 | 14 | 11.3 | BCF addition begun. |
| 0:05 | 16 | 11.1 | Addition of caustic solution begun. |
| 0:15 | 17 | 10.9 | About ¼ BCF added. |
| 0:25 | 18 | 10.8 | |
| 0:34 | 18 | 10.9 | About ½ BCF added. |
| 0:45 | 15 | 11.2 | |
| 0:50 | 14 | 11.4 | About ¾ BCF added. |
| 1:00 | 17 | 11.2 | |
| 1:10 | 16 | 11.3 | BCF addition complete. |
| 1:27 | 15 | 11.0 | Addition of caustic solution completed. |
| 1:29 | 16 | 11.0 | pH had stabilized. |
| 1:40 | 16 | 11.0 | HCl acid addition begun. |
| 2:03 | 13 | 1.7 | Intermittent HCl acid addition contained. |
| 2:25 | 14 | 1.7 | HCl acid addition completed; pH had stabilized. |

The amount of hydrochloric acid used was that necessary to reduce the pH to a stabilized value of 1.7. During the hydrochloric acid addition, a precipitate suddenly began to form at about pH 4.0, which froze into a near-solid mixture stopping the agitator. Approximately 600 cubic centimeters of ethyl acetate was added and the agitor was manually turned until it could move slowly under its own power. As the reaction mixture was stirred, the precipitate dissolved and permitted the agitator to move freely. After the pH had stabilized at 1.7, stirring was continued for about 15 minutes and then discontinued. When the reaction mixture had separated into two liquid phases, the bottom aqueous phase was drained off and reextracted with a further 300 cubic centimeters of ethyl acetate. The phases were separated and the organic phases from both extractions were combined and stored overnight over anhydrous magnesium sulfate. The solid phase was then removed by filtration and the filtrate was stripped in a Buchi rotary evaporator at about 40° C. and under the vacuum provided by a water aspirator. The solids were dried for 4 hours in a vacuum oven at about 45° C. and absolute pressures in the range of from about 3 to about 17 kilopascals, and then placed in a vacuum desiccator over phosphorous pentoxide for 16 hours at ambient temperature an an absolute pressure of about 13 to 27 pascals. The resulting product weighed 210.20 grams and melted in the range of 93° to 95° C. The yield of product was 83.0%, based of L-threonine. Nuclear magnetic resonance spectroscopy showed no moisture to be present. Analysis for purity was run by titration. Purity Found: 99.6%. The product was analyzed for NaCl. Found: 0.27% NaCl. The product was analyzed for moisture. Found: 0.31%$H_2O$. Four-tenths of a gram of the product was dissolved in 10 milliliters of acetic acid and the specific rotation $[\alpha]_D^{20}$ was determined. Found: −3.67°. Liquid chromatography showed the product to contain 99.9 area percent benzyloxycarbonyl-L-threonine when measured at 254 nanometers and 96.3 area percent N-benzyloxycarbonyl-L-threonine when measured at 210 nanometers. The infrared spectrum of the product matched the standard spectrum for N-benzyloxycarbonyl-L-threonine. The nuclear magnetic resonance spectrum of the product matched the standard spectrum for N-benzyloxycarbonyl-L-threonine, except that the former also indicated the presence of traces of an undefined impurity. The results of elemental analysis are shown in Table 2.

TABLE 2

| | % C | % H | % N | % O |
|---|---|---|---|---|
| Found | 56.83 | 6.03 | 5.44 | 31.56 |
| | 56.78 | 6.10 | 5.49 | 31.45 |
| Average Found | 56.81 | 6.07 | 5.47 | 31.51 |
| Theory | 56.91 | 5.97 | 5.53 | 31.59 |

The product appeared to be of analytical purity with all values in very good agreement.

EXAMPLE II

This example shows the effect of using 18-crown-6 ether as a phase transfer catalyst in the preparation of N-benzyloxycarbonyl-L-threonine.

A 1-liter, 5-necked reaction flask equipped as in Example I was charged with 59.56 grams of L-threonine (98%) and 300 grams of water. Forty grams of 50% aqueous sodium hydroxide solution was then added to convert the amino acid to the sodium salt. The reaction mixture then had a pH of about 10.8. To the reaction mixture was added 1.32 grams of 18-6 ether (99); no change in pH was observed. Over a period of 65 minutes, 87.0 grams of benzylchloroformate (98%) and about 40 grams of 50% aqueous sodium hydroxide solution were added as separate streams while the temperature was in the range of from 13° C. to 15° C. and while the pH was in the range of from about 10.8 to about 11.0 (mostly at about 10.9). After the pH had stabilized at about 11.0, the reaction mixture was stirred a further 75 minutes. Over a period of about 20 minutes, concentrated hydrochloric acid was added while maintaining the temperature of the reaction mixture in the range of from 5° C. to 8° C., until a pH of 1.5 was attained. The formation of a white precipitate was observed. Stirring of the reaction mixture was then continued for one hour, by the end of which time the pH had stabilized at about 1.6 and some crystal formation had occurred. Then, with rapid stirring, about 200 cubic centimeters of ethyl acetate was added. The precipitate dissolved, and rapid stirring was continued for about 5 minutes. The contents of the flask were charged to a 1-liter separatory funnel. When the reaction mixture had separated into two liquid phases, the bottom aqueous phase was drained off and the organic phase was bottled. The aqueous phase was reextracted with another 200 cubic centimeters of ethyl acetate, the phases were separated, and the organic phase was combined with that which was previously bottled. The combined organic phases were stored over anhydrous sodium sulfate overnight. The solid phase was then removed by filtration and the filtrate was stripped on a Buchi rotary evaporator at about 40° C. and under the vacuum provided by a water aspirator. The white solid which resulted was pulverized, placed in a drying dish and dried in a vacuum oven at 35° C. to 42° C. and absolute pressures in the range of from about 3 to about 17 kilopascals for 5¾ hours. The solids were stored overnight in a vacuum desiccator over phosphorous pentoxide at ambient temperature, dried in the vacuum oven under the previous conditions for 5 hours, and then again stored in the vacuum desiccator overnight. The resulting product weighed 118.0 grams and melted in the range of from 94° C. to 96° C. The yield of product was 93.2%, based on L-threonine. Analysis for purity was run by titration. Purity Found: 96.76%, 96.84%. Average Purity Found: 96.80%. The product was analyzed for NaCl. Found: 0.16%, 0.18% NaCl. Average Found: 0.17% NaCl. The product was analyzed for moisture. Found: 0.32%, 0.26% $H_2O$. Average Found: 0.29% $H_2O$. Four-tenths of a gram of the product was dissolved in 10 milliliters of acetic acid and the specific rotation was determined. Found: $-3.7°$, $-3.4°$. Average Found: $-3.55°$. Liquid chromatography showed the product to contain about 95 area percent N-benzyloxycarbonyl-L-threonine and about 3.7 area percent benzyl alcohol.

This example shows about a 12% increase in yield as compared to that of Example I. Also, the much more rapid pH stabilization at the end of benzylchloroformate addition in this as compared with that of Example I indicated that here benzyl chloroformate was consumed faster during its addition.

EXAMPLE III

This example shows the effect of using 18-crown-6 ether as a phase tranfer catalyst in the preparation of benzyloxycarbonyl-L-threonine in a more concentrated solution than in Example II.

A 1-liter, 5-necked reaction flask equipped as in Example I was charged with 59.56 grams of L-threonine (98%) and 200 grams of water. Forty grams of 50% aqueous sodium hydroxide solution was then added. The reaction mixture then had a pH of about 11.1. To the reaction mixture was added 1.32 grams of 18-crown-6 ether (99%). Over a period of 60 minutes, 87.0 grams of benzylchloroformate and about 40 grams of 50% aqueous sodium hydroxide solution were added as separate streams while the temperature was in the range of from 13° C. to 18° C. and while the pH was in the range of from about 10.8 to about 11.3. After the pH had stabilized at about 11.1, the reaction mixture was stirred a further 60 minutes without cooling. At the end of this period the temperature of the reaction mixture was about 17° C. and the pH was about 11.0. Over a period of about 25 minutes, 63 grams of concentrated hydrochloric acid was added with cooling such that the temperature rose from 5° C. to 9° C. Stirring was then continued for about 20 minutes during which time the pH was allowed to stabilize at a value of about 1.8 by making dropwise additions of concentrated hydrochloric acid as necessary. During this time the reaction mixture first thickened and then solidified causing the agitator to stop. Two hundred cubic centimeters of ethyl acetate was added and the agitator was manually turned until it could move slowly under its own power. As the reaction mixture was stirred, the precipitate dissolved and permitted the agitator to move freely. After the pH had stabilized at 1.8, stirring was discontinued. When the reaction mixture had separated into two liquid phases, the bottom agueous phase was drained off and reextracted with a further 200 cubic centimeters of ethyl acetate. The phases were separated and the organic phases from both extractions were combined and stored over anhydrous magnesium sulfate. The solid phase was removed by filtration and the filtrate was stripped in a rotating evaporator under the vacuum provided by a water aspirator. The solids were dried over two nights in a convection oven at 50° C. to 55° C. The resulting product weighed about 116.5 grams and melted in the range of from 93° C. to 94° C. The yield of the product was 92.0% based on L-threonine. Analysis for purity was run by titration. Purity Found: 96.68%, 96.74%. Average Found: 96.71%. The product was analyzed for NaCl. Found: 0.24%, 0.23% NaCl. Average Found: 0.24% NaCl. The product was analyzed for moisture. Found: 0.04%, 0.10% $H_2O$. Average Found: 0.07% $H_2O$. Four-tenths of a gram of the product was dissolved in 10 milliliters of acetic acid and the specific rotation was determined. Found: $-4.0°$, $-3.9°$. Average Found: $-3.95°$. Liquid chromatography showed the product to contain about 96.1 area percent N-benzyloxycarbonyl-L-threonine and about 1.6 area percent benzyl alcohol at 210 nanometers.

This example shows no major differences in results as compared with Example II. Again, the effect of the pH stabilizing very quickly after completion of the benzylchloroformate addition indicated the crown ether complex of the solution of the sodium salt of L-threonine is able to pass into the benzylchloroformate phase more quickly than the uncomplexed L-threonine sodium salt of Example I. This effect apparently permits a more rapid reaction.

EXAMPLE IV

This example shows the effect of using 18-crown-6 ether as a phase transfer catalyst in the preparation of N-benzyloxycarbonyl-L-threonine, but using a lesser amount of the 18-crown-6 ether than in Example II.

A 1-liter, 5-necked reaction flask equipped as in Example I was charged with 59.56 grams of L-threonine (98%) and 300 grams of water. Forty grams of 50% aqueous sodium hydroxide solution was then added to convert the amino acid to the sodium salt. The reaction mixture then had a pH of about 11.0. To the reaction mixture was added 0.66 gram of 18-crown-6 ether (99%). Over a period of 70 minutes, 87.0 grams of benzylchloroformate and about 40 grams of 50% aqueous sodium hydroxide solution were added as separate streams while the temperature was in the range of from 13° C. to 18° C. and while the pH was in the range of from about 10.8 to about 11.3. Within 3 to 4 minutes following the completion of the benzylchloroformate addition, the pH of the reaction mixture had stabilized at about 11.1. The reaction mixutre was then stirred for one hour. Then, over a period of about 25 minutes, about 63 grams of concentrated hydrochloric acid was added with cooling such that the temperature was maintained in the range of from 5° C. to 10° C. The formation of a white precipitate was observed. Stirring was then continued for about 20 minutes during which time the pH was allowed to stabilize at about 1.8 by making dropwise additions of concentrated hydrochloric acid as required. The reaction mixture was extracted with about 200 cubic centimeters of ethyl acetate. When the reaction mixture had separated into two liquid phases, the bottom aqueous phase was drained off and the organic phase was bottled. The aqueous phase was reextracted with another 200 cubic centimeters of ethyl acetate, the phases were separated, and the organic phase was combined with that which was previously bottled. The combined organic phases were stored over anhydrous magnesium sulfate overnight. The solid phase was then removed by filtration and the filtrate was stripped on a Buchi rotary evaporator using a warm water (about 40°) bath and the vacuum provided by a water aspirator. The white solid which resulted was pulverized, placed in a drying dish and dried in a convection oven at 55° C. overnight. The resulting product weighed 120.55 grams and melted in the range of from 97° C. to 98° C. The yield of product was 95.2%, based on L-threonine. Analysis for purity was run by titration. Purity Found: 97.66%, 98.14%. Average Purity Found: 97.90%. The product was analyzed for NaCl. Found: 0.31%, 0.32% NaCl. Average Found: 0.32% NaCl. The product was analyzed for moisture. Found: 0.03%, 0.08% $N_2O$. Average Found: 0.06% $H_2O$. Four-tenths of a gram of the product was dissolved in 10 milliliters of acetic acid and the specific rotation was determined. Found: $-3.7°$, $-3.9°$. Average Found: $-3.8°$. Liquid chromatography showed the product to contain 98.1 area percent N-benzyloxycarbonyl-L-threonine, 0.83 area percent benzyl alcohol and 0.1 area percent L-threonine at 210 nanometers.

This example shows that the reaction worked very well produced product in extremely high yield and purity using a lesser amount of 18-crown-6 ether than in Example II.

EXAMPLE V

This is a comparative example showing the effect of using a quaternary ammonium salt as a phase transfer catalyst in the preparation of N-benzyloxycarbonyl-L-threonine.

A 1-liter, 5-necked reaction flask equipped as in Example I was charged with 59.56 grams of L-threonine (98%) and 300 grams of water. Forty grams of 50% aqueous sodium hydroxide solution was then added to convert the amino acid to the sodium salt. The reaction mixture then had a pH of 11.1. To the reaction mixture was added 1.14 grams of benzyltriethylammonium chloride; no change in pH was observed. Over a period of one hour, 87.0 grams of benzylchloroformate (98+%) and about 40 grams of 50% aqueous sodium hydroxide solution were added as separate streams while the temperature was in the range of from 13° C. to 18° C. and while the pH was in the range of from 10.8 to about 12.0 (momentarily). The pH averaged about 11.4 during the addition. Within 2 minutes of completion of the additions, the pH had stabilized at a value of 11.2. After stirring for 90 minutes the reaction mixture was acidified, first with 6N hydrochloric acid to pH 3 and then dropwise with 12N hydrochloric acid to pH 1.5. The reaction mixture was stirred for 2 hours at a temperature of from 5° C. to 10° C., and then filtered. The separated solids were dried overnight in a vacuum oven at 40° C. and absolute pressures in the range of from about 3 to about 17 kilopascals. The resulting product weighed 105.6 grams, had a somewhat sticky consistency, softened in the range of from 84° C. to 91° C., and melted in the range of from 92° C. to 94° C. The yield of product was 83.4%, based on L-threonine. Analysis for purity was run by titration. Purity Found: 89.33%, 88.93%. Average Found: 89.13%. The product was analyzed for moisture. Found: 0.64%, 0.50% $H_2O$. Average Found: 0.57% $H_2O$. Liquid chromatography showed the product to contain aout 86.3 area percent N-benzyloxycarbonyl-L-threonine, about 9.4 area percent benzyl alcohol and about 4.3 area percent of other materials.

It appears that the catalytic decomposition of benzylchloroformate by the quaternary ammonium salt to produce benzyl chloride and carbon dioxide is a competing side reaction to the desired reaction, and that the benzyl chloride so produced is hydrolyzed to benzyl alcohol under the conditions of high pH present before acidification. These conclusions are reinforced by the large amount of contaminating benzyl alcohol observed to be present in the product.

EXAMPLE VI

This is a comparative example showing the effect of using no phase transfer catalyst in the preparation of N-benzyloxycarbonyl-L-serine.

A 1-liter, 5-necked reaction flask equipped as in Example I was charged with 42.04 grams of L-serine and 211 cubic centimeters of water. Thirty-two grams of 50% aqueous sodium hydroxide solution was then added dropwise over a period of about 10 minutes to convert the amino acid to the sodium salt. The reaction mixture then had a pH of about 11.1. The additions of 69.43 grams of benzylchloroformate (hereinafter "BCF") and about 32 grams of 50% aqueous sodium hydroxide solution (hereinafter "caustic solution") as separate streams were accomplished according to Table 3.

TABLE 3

| Time, hours:minutes | Temperature °C. | pH | Remarks |
| --- | --- | --- | --- |
| 0:00 | 12 | 11.1 | BCF addition begun. |
| 0:03 | 13 | 10.9 | Addition of caustic solution begun. |
| 0:10 | 16 | 10.8 | |
| 0:15 | 17 | 10.7 | |
| 0:20 | 21 | 11.5 | Cooling applied. |
| 0:25 | 18 | 11.1 | |
| 0:30 | 17 | 11.2 | |
| 0:35 | 15 | 11.1 | |
| 0:40 | 14 | 10.8 | |
| 0:45 | 14 | 10.9 | BCF addition completed. Continued adding a few cubic centimeters of caustic solution and then stopped the addition. |
| 0:50 | 13 | 9.8 | Added about 2 cubic centimeters of caustic solution to raise pH to 11.0. |
| 1:05 | 13 | 11.1 | pH has essentially stabilized. |

The reaction mixture was then stirred at a pH of about 11.0 for 30 minutes. After cooling the reaction to about 10° C., the pH was reduced to about 1.5 by the dropwise addition of concentrated hydrochloric acid with cooling over a period of about 15 minutes. A precipitate began to form between pH 6.1 and pH 5.5. Upon completion of the hydrochloric acid addition, the reaction mixture was stirred for 30 minutes and then left to stand overnight. Next, 175 cubic centimeters of ethyl acetate was added while the reaction mixture was stirred. After all of the solids had dissolved, the reaction mixture was placed in a separatory funnel. When the reaction mixture had separated into two liquid phases, the bottom aqueous phase was drained off, reextracted with a further 100 cubic centimeters of ethyl acetate and the phase were separated. The two organic phases resulting from the two extractions were each allowed to stand over anhydrous magnesium sulfate in separate containers for several hours. Each extract was then separately filtered and stripped of solvent in a rotating evaporator over a warm water bath and under the vacuum provided by a water aspirator. The two crops of solids resulting from the stripping were each dried overnight in a convection oven at 50° C. to 55° C. The dried first crop weighed 75.4 grams while the dried second crop weighed 2.0 grams. The total yield was 80.9%, based on L-serine. Nuclear magnesium resonance spectroscopy showed traces of water to be present. Both crops were dried for an additional 18 hours over phosphorous pentoxide. Nuclear magnetic resonance spectroscopy after the additional drying did not detect any water. The spectra were in agreement with the standard spectrum for N-benzyloxycarbonyl-L-serine. The results of various analyses are shown in Table 4.

TABLE 4

| Analysis | First Crop | Second Crop |
|---|---|---|
| Assay by titration | | |
| Found: | 94.67%, 94.59% | 98.77%, 98.93% |
| Average Found: | 94.63% | 98.85% |
| Sodium Chloride | | |
| Found: | 0.19%, 0.19% | 0.19%, 0.18% |
| Average Found: | 0.19% | 0.19% |
| Water | | |
| Found: | 0.26%, 0.21%, 0.26% | 0.24%, 0.24% |
| Average Found: | 0.24% | 0.24% |
| Specific Rotation | | |
| (0.4 gram/10 ml acetic acid) | | |
| Found: | +5.71°, +5.56° | Not Measured |
| Average Found | +5.64° | |

The results, expressed as area percents, of liquid chromatography are shown in Table 5.

TABLE 5

| Compound | First Crop, Area Percent | Second Crop, Area Percent |
|---|---|---|
| N—benzyloxycarbonyl-Lserine | | |
| At 210 nm: | 97.7 | 97.3 |
| At 254 nm: | 99.7 | 99.3 |
| Benzyl Alcohol | | |
| At 210 nm: | 0.1 | 0.1 |
| At 254 nm: | 0.1 | 0.1 |
| Other | | |
| At 210 nm: | 2.3 | 2.7 |
| At 254 nm: | 0.3 | 0.7 |

EXAMPLE VII

This example shows the effect of using 18-crown-6 ether as a phase transfer catalyst in the preparation of N-benzyloxycarbonyl-L-serine.

A 1-liter, 5-necked reaction flask equipped as in Example I was charged with 42.02 grams of L-serine and 211 cubic centimeters of water. While temperature of the reaction mixture was maintained in the range of from 10° C. to 15° C., the amino acid was converted to the sodium salt by the rapid dropwise addition of 32 grams of 50% aqueous sodium hydroxide solution. The reaction mixture then had a pH of 11.0. To the reaction mixture was added 0.3 grams of 18-crown-6 ether (99%); no change in pH was observed. The additions of 69.43 grams of benzylchloroformate (hereinafter "BCF") and about 12 grams of 50% aqueous sodium hydroxide solution (hereinafter "caustic solution") as separate streams were accomplished according to Table 6.

TABLE 6

| Time, hours:minutes | Temperature, °C. | pH | Remarks |
|---|---|---|---|
| 0:00 | 11 | 11.0 | BCF addition begun. |
| 0:02 | 11 | 10.95 | Addition of caustic solution begun. |
| 0:05 | 12 | 10.9 | |
| 0:10 | 14 | 10.8 | |
| 0:15 | 14 | 10.8 | |
| 0:20 | 15 | 10.9 | Cooling applied. |
| 0:25 | 17 | 11.0 | |
| 0:30 | 17 | 11.1 | |
| 0:35 | 20 | 11.2 | |
| 0:40 | 18 | 10.9 | |
| 0:45 | 17 | 10.7 | |
| 0:50 | 18 | 11.2 | |
| 0:53 | 16 | 11.0 | BCF addition completed. |
| 0:55 | Not Recorded | Not Recorded | Addition of caustic solution completed. |
| 0:56 | 14 | 11.3 | |

The pH stabilized within 2 to 3 minutes following completion of the benzylchloroformate addition. The reaction mixture was stirred at a pH of about 11.3 for 30 minutes. The pH was then reduced to about 1.5 by the dropwise addition of concentrated hydrochloric acid while stirring and cooling. A precipitate began to form between pH 6.0 and pH 5.6. Upon completion of the hydrochloric acid addition, the reaction mixture was stirred for about 30 minutes during which time it greatly thickened. Next, about 175 cubic centimeters of ethyl acetate was added while the reaction mixture was stirred. After all of the solids had dissolved, the reaction mixture was placed in a separatory funnel. When the reaction mixture had separated into two liquid phases, the bottom aqueous phase was drained off, reextracted with a further 100 cubic centimeters of ethyl acetate, and the phases were separated. The two organic phases resulting from the two extractions were each allowed to stand over anhydrous magnesium sulfate in separate containers for several hours. The respective extracts were warmed gently to dissolve any amounts of precipitate which had formed and were filtered to remove the magnesium sulfate. The filtrates were each stripped so solvent in a rotating evaporator using a warm water bath and the vacuum provided by a water aspirator. The two crops of the solids resulting from the stripping were each dried overnight in a convection overn at 50° C. to 55° C. and then further dried overnight over phosphorus pentoxide. The dried first crop weighed 84.6 grams while the dried second crop weighed 3.8 grams. The total yield was 92.4%, based on L-serine. The results of various analyses are shown in Table 7.

TABLE 7

| Analysis | First Crop | Second Crop |
|---|---|---|
| Assay by titration | | |
| Found: | 94.19%, 93.84%, 94.99% | 95.36%, 95.35% |
| Average Found: | 94.34% | 95.35% |
| Sodium Chloride | | |
| Found: | 0.22%, 0.66% | 0.59%, 0.57% |
| Average Found: | 0.44% | 0.58 |
| Water | | |
| Found: | 0.11%, 0.07%, 0.14% | 0.07%, 0.07%, 0.14% |
| Average Found: | 0.11% | 0.09% |
| Specific Rotation | | |
| (0.4 gram/10 ml acetic acid) | | |
| Found: | +5.32°,+5.66° | Not Measured |
| Average Found: | +5.49° | |

Liquid chromatography relative to an internal standard and measured at 254 nanometers showed the first crop to contain 93.9 relative percent N-benzyloxycarbonyl-L-serine and the second crop to contain 93.6 relative percent N-benzyloxycarbonyl-L-serine.

The very fast pH stabilization which occurred after conclusion of the benzylchloroformate addition indicates the sodium salt of the amino acid, when complexed with the crown ether, reacts faster with the benzylchlorofomate than does the sodium salt in the absence of a phase transfer catalyst. The data also indicate that the crown ether provides a specificity for reaction at the amino function relative to the hydroxy function.

EXAMPLE VIII

This example shows the effect of using 18-crown-6 ether as a phase transfer catalyst in the preparation of N-benzyloxycarbonyl-L-serine where the reaction of the disodium salt of the amino acid and the benzylchloroformate is conducted at pH values closer to the pK$_2$' of L-serine.

A 1-liter, 5-necked reaction flask equipped as in Example I was charged with 42.04 grams of L-serine and 210 cubic centimeters of water. While the temperature of the reaction was maintained in the range of from 10° C., the amino acid was converted to the sodium salt by the (rapid dropwise addition of 22.8 grams of 50% aqueous sodium hydroxide solution. The reaction mixture than had a pH of 9.7. To the reaction mixture was added 0.53 gram of 18-crown-6 ether (99%); no charge in pH was observed. The additions of 69.94 grams of enzylchoroformate (hereinafter "BCF") and about 41 grams of 50% aqueous sodium hydroxide solution (hereinafter "caustic solution") as separated streams were accomplished according to Table 8.

TABLE 8

| Time, hours:minutes | Temperature, °C. | pH | Remarks |
|---|---|---|---|
| 0:00 | 8 | 9.62 | BCF addition begun. |
| 0:05 | 9 | 9:60 | |
| 0:10 | 9 | 9.59 | |
| 0:12 | 10 | 9.59 | Added a few drops of caustic solution to temporarfly raise pH to 9.75; slow addition of caustic solution begun. |
| 0:20 | 13 | 9:48 | |
| 0:23 | 15 | 9:50 | About ½ BCF added. |
| 0:28 | 16 | Not Recorded | |
| 0:34 | 16 | 9.55 | |
| 0:42 | 17 | 9.48 | |
| 0:49 | 15 | 9.51 | |
| 0:58 | 14 | 9.50 | |
| 1:05 | 15 | 9.48 | BCF addition completed. |
| 1:12 | 14 | 9.56 | Addition of caustic solution completed. |
| 1:20 | 13 | 9.58 | pH has stabilized. |

The reaction mixture was stirred at a pH of about 9.58 for 30 minutes. The pH was then reduced to about 1.5 by the dropwise addition of concentrated hydrochloric acid with stirring over a period of 19 minutes while the temperature of the reaction mixture was maintained in the range of from 7° C. to 10° C. A precipitate began forming at a pH of about 5.8. Upon completion of the hydrochloric acid addition, the reaction mixture was stirred for about 30 minutes at a pH of about 1.6, and then 200 cubic centimeters of ethyl acetate was added with stirring. After all the solids had dissolved, the reaction mixture was placed in a separatory funnel. When the reaction mixture had separated into two liquid phases, the bottom aqueous phase was drained off, reextracted with a further 200 cubic centimeters of ethyl acetate, and the phases were separated. The two organic phases resulting from the two extractions were each allowed to stand over anhydrous magnesium sulfate in separate containers for several hours. The respective extracts were warmed gently to dissolve any amounts of precipitate which had formed and were filtered to remove the magnesium sulfate. The filtrates were each stripped of solvent in a rotating evaporator using a warm water bath and the vacuum provided by a water aspirator. The two crops of solids resulting from the stripping were each dried overnight in a convection oven at 50° C. to 55° C. and then further dried overnight over phosphorous pentoxide. The dried first crop weighed 84.2 grams while the second crop weighed 2.0 grams. The total yield was 90.1%, based on L-serine. The results of various analyses are shown in Table 9.

TABLE 9

| Analysis | First Crop | Second Crop |
|---|---|---|
| Assay by titration | | |
| Found: | 95.92%, 96.00% | 94.59%, 94.83% |
| Average Found: | 95.96% | 94.71% |
| Sodium Chloride | | |
| Found: | 0.40%, 0.40% | 0.09, 0.10% |
| Average Found: | 0.40% | 0.10% |
| Water | | |
| Found: | 0.17%, 0.25% | 0.05, 0.04% |
| Average Found: | 0.21% | 0.05% |

Liquid chromatography at 210 nanometers showed the first crop and the second crop to each contain 99.2 area percent N-benzyloxycarbonyl-L-serine.

The data demonstrate that by maintaining the pH of the reaction mixture only slightly above the literature pK$_2$' value for L-serine (pK$_2$' 9.15) during the reaction of the sodium salt of the amino acid, the competing hydrolysis of benzylchloroformate and the concomitant formation of benzyl alcohol are reduced.

Although the present invention has been described with reference to specific details of certain embodiments thereof, it is not intended that such details should be regarded as limitations upon the scope of the invention except insofar as they are included in the accompanying claims.

I claim:

1. In the method wherein alkali metal salt of a amino acid which is devoid of tertiary amino groups and quaternary ammonium groups, and which contains in addition to a primary amino group and at least one carboxylate anion, at least one functional group selected from the class consisting of hydroxyl, additional primary amino, secondary amino, primary imido, and primary amido, is reacted with benzylhaloformate selcted from the class consisting of ring-substituted benzylchloroformate, ring-unsubstituted benzylchloroformate, ring-substituted benzylbromoformate, and ring-unsubstituted benzylbromoformate in a polyphase reaction mixture comprising an organic liquid phase and an queous liquid phase to produce alkali metal salt of an N-benzyloxycarbonyl amino acid in which the benzyl is substituted or unsubstituted and which contains said functional group, the improvement comprising conducting the reaction in the presence of a phase-transfer reagent comprising crown ether, silacrown ether, or a mixture thereof.

2. The method of claim 1 wherein said phase-transfer reagent is represented by the formula

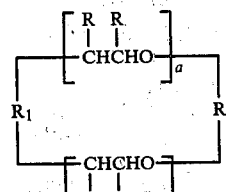

wherein
a. $R_1$ is

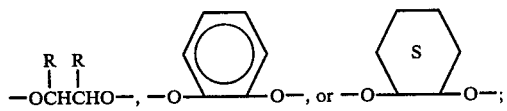

b. $R_2$ is

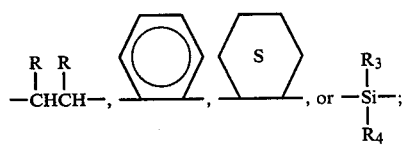

c. $R_3$ is methyl, ethyl, methoxy, ethoxy, vinyl, an organic polymeric substrate, or an inorganic polymeric substrate;
d. $R_4$ is methyl, ethyl, methoxy, or ethoxy;
e. each individual R of said phase-transfer reagent is independently hydrogen, methyl, ethyl, methoxy, ethoxy, vinyl, or phenyl;
f. The value of a is in the range of from 0 to 4; and
g. the value of b is in the range of from 1 to 4.

3. The method of claim 1 wherein said phase-transfer reagent is crown ether selected from the class consisting of 12-crown-4, 15-crown-5 and 18-crown-6.

4. The method of claim 1 wherein said phase-tranfer reagent is 18-crown-6.

5. A method comprising:
a. reacting alkali metal salt of an amino acid which is devoid of tertiary amino groups and quaternary ammonium groups, and which contains in addition to a primary group and at least one carboxylate anion, at least one functional group seclected from the class consisting of hydroxyl, additional primary amino, secondary amino, primary imido, and primary amido, with benzylhaloformate selected from the class consisting of ring-substituted benzylchloroformate, ring-unsubstituted benzylchloroformate, ring-substituted benzylbromoformate and ring-unsubstituted benzylbromoformate in a polyphase reaction mixture comprising an organic liquid phase and an aqueous liquid phase and in the presence of a phase-transfer reagent comprising crown ether silacrown ether, or a mixture thereof to produce alkali metal salt of an N-benzyloxycarbonyl amino acid in which the benzyl is substituted or unsubstituted; and b. acidifying said alkali metal salt of said N-benzyloxycarbonyl amino acid to produce N-benzyloxycarbonyl amino acid in which the benzyl is substituted or unsubstituted and which contains said functional group.

6. The method of claim 5 wherein said phase-transfer reagent is represented by the formula

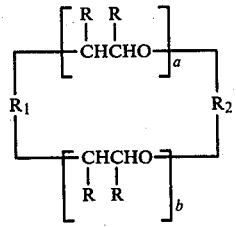

a. $R_1$ is

b. $R_2$ is

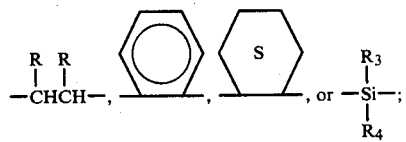

c. $R_3$ is methyl, ethyl, methoxy, ethoxy, vinyl, an organic polymeric substrate, or an inorganic polymeric substrate;
d. $R_4$ is methyl, ethyl, methoxy, or ethoxy;
d. each individal R of said phase-transfer reagent is independently hydrogen, methyl, ethyl, methoxy, ethoxy, vinyl, or phenyl;
f. The value of a is in the range of from 0 to 4and
g. the value of b is in the range of from 1 to 4.

7. The method of claim 5 wherein said phase-transfer reagent is crown ether selected from the class consisting of 12-crown-4, 15-crown-5 and 18-crown-6.

8. The method of claim 5 wherein said phase-transfer reagent is 18-crown-6.

9. The method of claim 5 wherein said benzylhaloformate is ring-unsubstituted benzylchloroformate.

10. The method of claim 5 wherein said functional group is hydroxyl.

11. The method of claim 5 wherein said alkali metal salt of an amino acid which is reacted with said benzylhaloformate is alkali metal salt of threonine or alkali metal salt of serine.

12. The method fo claim 5 wherein the pH of the aqueous liquid phase is maintained in the range of from about $pK_2'$ to about $(pK_2' + 1.5)$ during the reaction of said alkali metal salt of said amino acid and said benzylhaloformate, where $pK_2'$ is the $pK_2'$ value of the amino acid whose alkali metal salt is employed as a reactant.

13. The method of claim 5 wherein the pH of the aqueous liquid phase is maintained in the range of from about $pK_2'$ to about $(pK_2' + 1)$ during the reaction of said alkali metal salt of said amino acid and said benzylhaloformate, where $pK_2'$ is the $pK_2'$ value of the amino acid whose alkali metal salt is employed as a reactant.

14. The method of claim 5 wherein said polyphase reaction mixture comprises an organic liquid phase, an aqueous liquid phase, and a solid phase.

15. The method of claim 5 wherein said alkali metal is lithium, sodium, or potassium.

16. The method of claim 5 wherein said alkali metal is sodium.

17. The method of claim 5 wherein the reaction of said alkali metal salt of an amino acid and said benzylhaloformate is conducted at temperatures in the range of from about $-10°$ C. to about $+60°$ C.

18. The method of claim 5 wherein the final pH of the reaction mixture resulting from said acidification is in the range of from about 1 to about 4.

19. The method of claim 5 wherein said acidification is conducted using hydrochloric acid.

20. The method of claim 5 wherein sodium or potassium salt of an amino acid which is devoid of tertiary amino groups and quaternary ammonium groups, and which contains a hydroxyl group is reacted with benzylchloroformate in a polyphase reaction mixture and in the presence of 18-crown-6 ether to produce sodium or potassium salt of benzyloxycarbonyl amino acid; and wherein said sodium or potassium salt of said benzyloxycarbonyl amino acod os acidified with hydrochloric acid to produce N-benzyloxycarbonyl amino acid containing a hydroxyl group.

* * * * *

UNITED STATES PATENT AND TRADEMARK OFFICE
CERTIFICATE OF CORRECTION

PATENT NO.  : 4,484,001

DATED       : November 20, 1984

INVENTOR(S) : James A. Krogh

It is certified that error appears in the above-identified patent and that said Letters Patent is hereby corrected as shown below:

Claim 1, line 13, "que-" should be --aque- --;

Claim 5(a), line 4, "primary group" should be --primary amino group--;

Claim 5(a), line 16, insert a comma after "crown ether";

Claim 6(d), (second instance) "d" should be --e--;

Claim 6(f), line 1, "4and" should be --4; and--;

Claim 20, line 9, "acod os" should be --acid is--.

Signed and Sealed this

Second Day of July 1985

[SEAL]

Attest:

DONALD J. QUIGG

Attesting Officer    Acting Commissioner of Patents and Trademarks